United States Patent [19]
Kakihana et al.

[11] Patent Number: 5,965,568
[45] Date of Patent: *Oct. 12, 1999

[54] COMPOSITION FOR INHIBITING PRODUCTION OR SECRETION OF AMYLOID β PROTEIN TO TREAT DOWN'S SYNDROME

[75] Inventors: Mitsuru Kakihana, Kobe; Takuo Kosaka, Nerima-ku; Akinobu Nagaoka, Kawanishi; Giichi Goto, Toyono-gun, all of Japan

[73] Assignee: Takeda Chemical Industries, Ltd., Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/646,354
[22] PCT Filed: Feb. 8, 1996
[86] PCT No.: PCT/JP96/00265
  § 371 Date: May 10, 1996
  § 102(e) Date: May 10, 1996
[87] PCT Pub. No.: WO96/25161
  PCT Pub. Date: Aug. 22, 1996

[30] Foreign Application Priority Data

Feb. 15, 1995 [JP] Japan .................................. 7-026687

[51] Int. Cl.$^6$ .................................................. A61K 31/44
[52] U.S. Cl. .................................................. 514/283
[58] Field of Search .................................... 514/283

[56] References Cited

U.S. PATENT DOCUMENTS

| | | | |
|---|---|---|---|
| 4,035,370 | 7/1977 | Lorincz et al. | 260/293.53 |
| 4,400,514 | 8/1983 | Szantay et al. | 546/51 |
| 5,428,035 | 6/1995 | Teleha | 514/234.5 |

FOREIGN PATENT DOCUMENTS

| | | |
|---|---|---|
| 0 305 181 A3 | 3/1989 | European Pat. Off. |
| 0 361 888 A3 | 4/1990 | European Pat. Off. |
| 94/17197 | 8/1994 | WIPO |

OTHER PUBLICATIONS

Outline of Calan Tablets (in Japanese) and its English translation, Feb. 1987.

C. Nicholson, "Nootropics and metabolically active compounds in Alzheimer's disease", vol. 17, Biochemical Society Transactions, pp. 83–85, Feb. 1989.

Masashi Sasa, "Drugs for Therapy of Dementia", The Japanese Journal of Pharmacology, vol. 49, Official Publication of the Japanese Pharmacological Society, Mar. 25–28, 1989.

R. Bartus et al., "Behavioral and Pharmacological Studies Using Animal Models Aging: Implications for Studying and Treating Dementia of Alzheimer's Type", vol. 15, Banbury Report, pp. 207–218, 1983.

G. Caporaso et al., "Protein Phosphorylation Regulates Secretion of Alzheimer β/A4 Aryloid Precursor Protein", Proc. Natl. Acad. Sci., vol. 89, pp. 3055–3059, Apr. 1, 1992.

I. Hindmarch, "Efficacy and Tolerance of Vinpocetine in Ambulant Patients Suffering from Mild to Moderate Organic Psychosyndromes", vol. 6, International Clinical Psychopharmacology, pp. 31–43, 1991.

CA vol. 110, No. 51211 Notvest et al., 1987.

*Primary Examiner*—Theodore J. Criares
*Attorney, Agent, or Firm*—Wenderoth, Lind & Ponack, L.L.P.

[57] ABSTRACT

A pharmaceutical composition for inhibiting production or secretion of amyloid β protein, which comprises a compound of the formula (I):

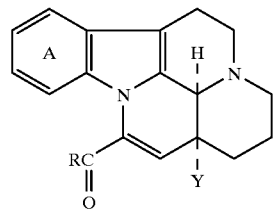

wherein ring A is an optionally substituted benzene ring, R represents OR$^1$,

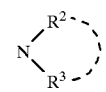

or SR$^1$, wherein R$^1$, R$^2$ and R$^3$ are the same or different and each is selected from a hydrogen atom, an optionally substituted hydrocarbon group or R$^2$ and R$^3$, taken together with the adjacent nitrogen atom, form an optionally substituted nitrogen-containing heterocyclic group, and Y is an optionally substituted alkyl group, or a pharmaceutically acceptable salt thereof, if necessary, with a pharmaceutically acceptable excipient, carrier or diluent.

4 Claims, 4 Drawing Sheets

** p<0.01

COMPOSITION FOR INHIBITING PRODUCTION OR SECRETION OF AMYLOID β PROTEIN TO TREAT DOWN'S SYNDROME

This application is a 371 of PCT/JP 96/00265 filed Feb. 8, 1996.

BACKGROUND OF THE INVENTION

1. Field of the Invention

The present invention relates to a composition, particularly a pharmaceutical composition, for inhibiting production or secretion of an amyloid β protein. The composition is effective in treating degenerative brain disorders such as senile dementia, Alzheimer's disease, Down's syndrome, etc., amyloid angiopathy, brain disorders caused by amyloid β protein in cerebrovascular diseases, etc.

2. Description of Related Art

Alzheimer's disease is a neurodegenerative disease characterized by senile plaque and neurofibrillar tangles as well as degeneration and loss of neurons. The senile plaques, which are most characteristic of the disease, are deposits composed of amyloid β protein (hereinafter sometimes abbreviated as Aβ) derived from β-amyloid precursor protein (hereinafter sometimes abbreviated as βAPP) as a major component (Biochem. Biophys. Res. Commun., 122, 1131 (1984)), apolipoprotein E (Brain Res., 541, 163 (1991)) and heparan sulfate proteoglycan (Am. J. Pathol., 133, 456 (1988)), etc.

Aβ of 40 or 42 amino acids exhibits toxicity to neurons (Science, 250, 279 (1990)), and induces neurofibrillar changes (Proc. Natl. Acad. Sci., 90, 7789 (1993)). In patients with familial Alzheimer's disease, mutations on the βAPP gene are observed (Lancet, 337, 978 (1991); Nature, 349, 704 (1991); Science, 254, 97 (1991); Nature, 354, 844 (1991)). Cells containing such mutated gene produce and secrete an increased amount of Aβ (Nature, 360, 672 (1992); Science, 259, 514 (1993); Science, 264, 1336 (1994)).

Patients with Down's syndrome showing cerebral changes pathologically similar to those of Alzheimer's disease (Proc. Natl. Acad. Sci., 82, 4245 (1985)) have trisomy 21 (i.e., three chromosome 21s containing the βAPP gene) and promoted expression of the βAPP gene and βAPP protein in the brain (Science, 235, 880 (1987); N. Eng. J. Med., 320, 1446 (1989)).

Based on these findings, the participation of the abnormal production or secretion of Aβ in the onset of Alzheimer's disease is considered to be highly important.

It is believed that βAPP is metabolized with proteases called α- and β-secretases through two pathways (Science, 248, 492 (1990); Science, 248, 1122 (1990); Science, 255, 726 (1992); Science, 255, 728 (1992); Nature, 357, 500 (1992)). When βAPP is metabolized with α-secretase, βAPP is cleaved at position 16 of Aβ, Aβ is not produced, and the N-terminal fragment of βAPP is released out of the cells as secreted βAPP, which acts as a neurotrophic factor (Neuron, 10, 243–254 (1993)). On the other hand, when βAPP is cleaved with β-secretase, a C-terminal fragment of βAPP containing Aβ is produced. However, it is unclear where the C-terminal fragment or Aβ is produced in the cells and how Aβ is secreted out of the cells. In addition, although candidate enzymes for α- and β-secretases have been reported (J. Biol. Chem., 268, 16699 (1993); Biochemistry, 33, 192 (1994)), they have not identified.

It has been reported that some compounds, phorbol esters (Proc. Natl. Acad. Sci., 89, 3055 (1992)) and M1 muscarinic receptor agonist, carbacol (Science, 258, 302 (1992)) increase the secreted βAPP and inhibit Aβ production or secretion in in vitro various cells. However, these compounds are unsatisfactory in terms of efficacy, safety, etc.

SUMMARY OF THE INVENTION

Figure 1:
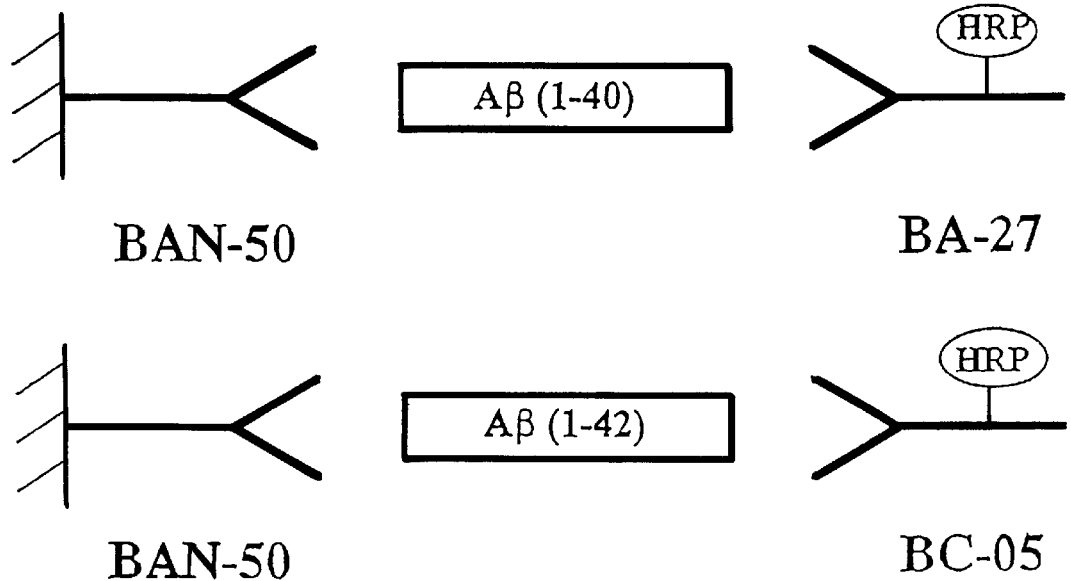
FIG. 1 is a diagram showing combinations of antibodies used in the EIA system. HRP means horseradish peroxidase.

The present inventors have intensively studied to find an inhibitor of Aβ production or secretion. As a result, it has been found that vinpocetine (CALAN™) or a derivative thereof has inhibitory activity against Aβ production or secretion.

Vinpocetine or its derivative is a known compound disclosed in JP-B 51-32640 (U.S. Pat. No. 4,035,370) and JP-B 2-27352 (U.S. Pat. No. 4,400,514). However, these publications only disclose cerebro-vasodilative, systemic-vasodilative and hypotensive activities of the compound, and fails to teach or suggest inhibitory activity against Aβ production or secretion.

The present invention provides a pharmaceutical composition for inhibiting production or secretion of amyloid β protein, particularly for preventing or treating Alzheimer's disease, which comprises a compound of the formula (I):

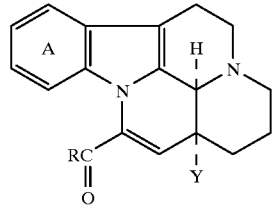

wherein ring A is an optionally substituted benzene ring, R represents $OR^1$,

or $SR^1$,
wherein $R^1$, $R^2$ and $R^3$ are the same or different and each is selected from a hydrogen atom, an optionally substituted hydrocarbon group or $R^2$ and $R^3$, taken together with the adjacent nitrogen atom, form an optionally substituted nitrogen-containing heterocyclic group, and Y is an optionally substituted alkyl group, or a pharmaceutically acceptable salt thereof, if necessary, with a pharmaceutically acceptable excipient, carrier or diluent.

DETAILED DESCRIPTION OF THE PREFERRED EMBODIMENT(S)

"Hydrocarbon group" of the term "optionally substituted hydrocarbon group" used in this specification include, among others, aliphatic hydrocarbon groups, monocyclic saturated hydrocarbon groups and aromatic hydrocarbon groups. The carbon number of the hydrocarbon group is preferably 1 to 16. An alkyl group, an alkenyl group, an alkynyl group, a cycloalkyl group and an aryl group are exemplified.

"Alkyl group" is preferably a lower alkyl group, for example, $C_{1-6}$ alkyl groups such as methyl, ethyl, propyl, isopropyl, butyl, isobutyl, sec-butyl, tert-butyl, pentyl and hexyl are used.

"Alkenyl group" is preferably a lower alkenyl group, for example, $C_{2-6}$ alkenyl groups such as vinyl, 1-propenyl, allyl, isopropenyl, butenyl and isobutenyl are used.

"Alkynyl group" is preferably a lower alkynyl group, for example, $C_{2-6}$ alkynyl groups such as ethynyl and 1-propynyl are used.

"Cycloalkyl group" is preferably a lower cycloalkyl group, for example, $C_{3-6}$ cycloalkyl groups such as cyclopropyl, cyclobutyl, cyclopentyl and cyclohexyl are used.

"Aryl group" is preferably $C_{6-14}$ aryl groups such as phenyl, xylyl, 1-naphthyl, 2-naphthyl, biphenylyl, 2-indenyl and 2-anthlyl. Among others, a phenyl group, for example, is used.

Examples of the substituents, which "hydrocarbon group" of "optionally substituted hydrocarbon group" may optionally have, include halogen atoms, (e.g. fluorine, chlorine, bromine and iodine), a nitro group, a cyano group, a hydroxyl group, optionally halogenated $C_{1-6}$ alkyl groups (e.g. methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trif luoropentyl, hexyl and 6,6,6-trifluorohexyl), lower alkoxy groups (e.g. $C_{1-6}$ alkoxy groups such as methoxy, ethoxy, propoxy, isopopoxy, butoxy, isobutoxy, pentyloxy and hexyloxy), an amino group, mono-lower alkylamino groups (e.g. mono-$C_{1-6}$ alkylamino groups such as methylamino and ethylamino), di-lower alkylamino groups (e.g. di-$C_{1-6}$ alkylamino groups such as dimethylamino and diethylamino), a carboxyl group, lower alkylcarbonyl groups (e.g. $C_{1-6}$ alkyl-carbonyl groups such as acetyl and propionyl), lower alkoxycarbonyl groups (e.g. $C_{1-6}$ alkoxy-carbonyl groups such as methoxycarbonyl, ethoxycarbonyl, propoxycarbonyl and butoxycarbonyl), a carbamoyl group, mono-lower-alkylcarbamoyl groups (e.g. mono-$C_{1-6}$ alkylcarbamoyl groups such as methylcarbamoyl and ethylcarbamoyl), di-lower alkylcarbamoyl groups (e.g. di-$C_{1-6}$ alkylcarbamoyl groups such as dimethylcarbamoyl and diethylcarbamoyl), arylcarbamoyl groups (e.g. $C_{6-10}$ arylcarbamoyl groups such as phenylcarbamoyl and naphthylcarbamoyl), aryl groups (e.g. $C_{6-10}$ aryl groups such as phenyl and naphthyl) and aryloxy groups (e.g. $C_{6-10}$ aryloxy groups such as phenyloxy and naphthyloxy), optionally halogenated lower alkylcarbonylamino groups (e.g. optionally halogenated $C_{1-6}$ alkyl-carbonylamino groups such as acetylamino, trifluoroacetylamino). "Hydrocarbon group" of "optionally substituted hydrocarbon group" may optionally have 1 to 5, preferably 1 to 3, of these substituents. When the number of the substituents is two or more, they may be the same one or different from one another.

Examples of "nitrogen-containing heterocyclic group" formed by $R^2$, $R^3$ and the adjacent nitrogen atom include 4- to 8-membered heterocyclic groups each of which contains at least one nitrogen atom and may contain 1 to 3, preferably 1 to 2, oxygen atoms, sulfur atoms, etc. in addition to carbon atoms as the ring-constituting atoms, and their benzo-condensed groups.

Specific examples of the nitrogen-containing heterocyclic groups include aromatic heterocyclic groups such as 1-pyrrolyl, 1-imidazolyl, 1-indolyl, 1-pyrazolyl, 2-isoindolyl, 1-indazolyl, etc.; cyclic amino groups such as morpholino, piperidino, 1-piperazinyl optionally having a substituent on the nitrogen atom at the 4-position, 1-pyrrolidinyl, 1-pyrazolidinyl, 1-azepinyl, etc.; or their benzo-condensed groups (e.g. 1-indolinyl, 2-isoindolinyl, 1,2,3,4-tetrahydroquinolin-1-yl, 1,2,3,4-tetrahydroisoquinolin-2-yl, 3-benzazepin-3-yl); lactam or imido groups such as phthalimido, succinimido, 2-pyrrolidon-1-yl, 2-pyridon-1-yl, 2-quinolon-1-yl, etc.

"Nitrogen-containing heterocyclic group" formed by $R^2$, $R^3$ and the adjacent nitrogen atom may have the same substituents as those described above for "optionally substituted hydrocarbon group". The benzo-condensed group may have one or more substituents at any possible position on the benzene ring. The substituents are selected from halogen atoms (e.g. fluorine, chlorine, bromine, iodine, etc.), lower alkylendioxy groups (e.g. $C_{1-3}$ alkylenedioxy groups such as methylenedioxy, ethylenedioxy, etc.), a nitro group, a cyano group, optionally halogenated lower alkyl groups (e.g. optionally halogenated $C_{1-6}$ alkyl groups such as chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl), optionally halogenated lower alkoxy groups (e.g. optionally halogenated $C_{1-6}$ alkoxy groups such as chloromethoxy, difluoromethoxy, trichloromethoxy, trifluoromethoxy, ethoxy, 2-bromoethoxy, 2,2,2-trifluoroethoxy, pentafluoroethoxy, propoxy, 3,3,3-trifluoropropoxy, isopropoxy, butoxy, 4,4,4-trifluorobutoxy, isobutoxy, sec-butoxy, tert-butoxy, pentyloxy, isopentyloxy, neopentyloxy, 5,5,5-trifluoropentyloxy, hexyloxy and 6,6,6-trifluorohexyloxy), optionally halogenated lower alkylthio groups (e.g. optionally halogenated $C_{1-6}$ alkylthio groups such as chloromethylthio, difluoromethylthio, trichloromethylthio, trifluoromethylthio, ethylthio, 2-bromoethylthio, 2,2,2-trifluoroethylthio, pentafluoroethylthio, propylthio, 3,3,3-trifluoropropylthio, isopropylthio, butylthio, 4,4,4-trifluorobutylthio, isobutylthio, sec-butylthio, tert-butylthio, pentylthio, isopentylthio, neopentylthio, 5,5,5-trifluoropentylthio, hexylthio and 6,6,6-trifluorohexylthio), a hydroxyl group, an amino group, mono-lower alkylamino groups (e.g. mono-$C_{1-6}$ alkylamino groups such as methylamino, ethylamino, propylamino, isopropylamino, butylamino, etc.), di-lower alkylamino groups (e.g., di-$C_{1-6}$ alkylamino groups such as dimethylamino, diethylamino, dipropylamino, dibutylamino, etc.), a carboxyl group, lower alkoxycarbonyl groups (e.g., $C_{1-6}$ alkoxycarbonyl groups such as methoxycarbonyl, ethoxycarbonyl, propoxycarbonyl, butoxycarbonyl, etc.) and a carbamoyl group.

"Alkyl group" of the term "optionally substituted alkyl group" used in this specification includes, for example, $C_{1-15}$ alkyl groups such as methyl, ethyl, propyl, isopropyl, butyl, isobutyl, sec-butyl, tert-butyl, pentyl, isopentyl, neopentyl, hexyl, heptyl, octyl, nonyl, decyl, undecyl, dodecyl, tridecyl, tetradecyl, pentadecyl, preferably lower ($C_{1-6}$) alkyl groups such as methyl, ethyl, propyl, isopropyl, butyl, isobutyl, sec-butyl and tert-butyl. The alkyl group may optionally have 1 to 3 substituents which, for example, the above-mentioned "hydrocarbon group" may optionally have.

The term "optionally substituted benzene ring" used in this specification means a benzene ring which optionally have, at any possible position, one to three substituents selected from halogen atoms (e.g. fluorine, chlorine, bromine and iodine), optionally substituted hydrocarbon groups, optionally substituted hydroxyl groups (preferably, optionally substituted lower ($C_{1-6}$) alkoxy groups such as methoxy, ethoxy, propoxy and isopropoxy), an optionally substituted amino group, amido groups (e.g. $C_{1-6}$ acylamino groups such as acetamido), and lower alkylenedioxy groups (e.g. $C_{1-6}$ alkylenedioxy groups such as methylenedioxy, ethylenedioxy).

The term "optionally substituted amino group" used in this specification means an amino group which may optionally have, as the substituents, one or two of the above-mentioned "optionally substituted hydrocarbon group" for example. Preferable examples of the substituents, which this "amino group" may optionally have, include an optionally substituted $C_{1-6}$ alkyl group and an optionally substituted $C_{6-10}$ aryl group. The substituents of the alkyl or aryl group are, for example, the same substituents which above-mentioned "hydrocarbon group" may optionally have.

The term "optionally substituted hydroxyl group" used in this specification means a hydroxyl group which may have, in place of the hydrogen atom of the hydroxyl group, one "optionally substituted hydrocarbon group" mentioned above. preferable examples of "substituted hydroxyl group" include a hydroxyl group substituted with one lower alkyl group. Examples of the "lower alkyl group" include $C_{1-6}$ alkyl groups such as methyl, ethyl, propyl, isopropyl, butyl, isobutyl, sec-butyl and tert-butyl. The substituents which "lower alkyl group" may optionally have are, for example, the same ones as the above-mentioned "hydrocarbon group" may optionally have.

The "optionally substituted hydrocarbon group" includes the same ones as those mentioned above. When the number of the substituents is two or more, they may be the same one or different from one another.

In the above formulae, ring A is an optionally substituted benzene ring. Preferable examples of ring A include an unsubstituted benzene ring or benzene rings having 1 to 3 substituents selected from halogen atoms (e.g. fluorine and chlorine), $C_{1-6}$ alkyl groups (e.g. methyl and ethyl), $C_{1-6}$ alkoxy groups (e.g. methoxy and ethoxy) which may have a $C_{6-10}$ aryl group, hydroxyl group and mono-$C_{1-6}$ alkylamino group, especially preferable one being, for example, a benzene ring substituted with one, for example, $C_{1-6}$ alkoxy group (e.g. methoxy).

Among others, ring A is preferably an unsubstituted benzene ring or benzene rings having 1 to 3 halogen atoms (e.g. fluorine and chlorine). More preferably, ring A is a benzene ring.

In the above formulae, R represents $OR^1$,

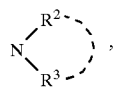

or $SR^1$, wherein $R^1$, $R^2$ and $R^3$ are the same or different and each is selected from a hydrogen atom, an optionally substituted hydrocarbon group or $R^2$ and $R^3$, taken together with the adjacent nitrogen atom, form an optionally substituted nitrogen-containing heterocyclic group.

Preferable examples of "hydrocarbon group" shown by $R^1$, $R^2$ and $R^3$ include alkyl groups (e.g., $C_{1-6}$ alkyl groups such as methyl, ethyl, propyl and isopropyl), alkenyl groups (e.g. $C_{2-6}$ alkenyl groups such as vinyl), alkynyl groups (e.g. $C_{2-6}$ alkynyl groups such as ethynyl), cycloalkyl groups (e.g. $C_{3-6}$ cycloalkyl groups such as cyclopropyl, cyclobutyl, cyclopentyl and cyclohexyl) and aryl groups (e.g. $C_{6-14}$ aryl groups such as phenyl). Among others, alkyl groups (e.g. $C_{1-6}$ alkyl groups such as methyl) and cycloalkyl groups (e.g. $C_{3-6}$ cycloalkyl groups such as cyclopropyl) are preferably used. The "alkyl group", "alkenyl group", "alkynyl group", "cycloalkyl group", and "aryl group" may optionally have, for example, 1 to 5, preferably 1 to 3 substituents, which the above-mentioned "hydrocarbon group" may optionally have, (preferably halogen atoms such as fluorine).

A preferable example of R is $OR^1$ wherein $R^1$ is an alkyl group, more preferably, $R^1$ is ethyl.

In the above formulae, Y is an optionally substituted alkyl group. Preferable examples of Y are lower ($C_{1-6}$) alkyl groups (e.g. methyl, ethyl, propyl, isopropyl, butyl, isobutyl, sec-butyl and tert-butyl). More preferable examples of Y include ethyl.

Preferable examples of the compound (I) include the compound of the formula (II):

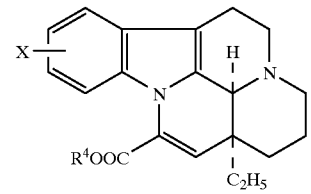

wherein X is hydrogen or halogen and $R^4$ is alkyl, and the preferable compounds may be, if necessary, used with a pharmaceutically acceptable excipient, carrier or diluent.

The halogen represented by X in the formula (II) includes fluorine, chlorine, bromine, and iodine. The alkyl represented by $R^4$ includes, for example, alkyl having 1 to 6 carbon atoms, such as methyl, ethyl, propyl, isopropyl, butyl, isobutyl, t-butyl, pentyl, and hexyl. Methyl and ethyl are preferred. In particular, vinpocetine, i.e. the compound of the formula (II) wherein X is hydrogen and $R^4$ is ethyl, is preferred.

The pharmaceutically acceptable salts of the compound of the formula (I) include, for example, salts with inorganic acids such as hydrochloric acid, hydrobromic acid, nitric acid, sulfuric acid, and phosphoric acid, salts with organic acids such as formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid.

The compound of the formula (I) or a pharmaceutically acceptable salt thereof can be prepared by known methods disclosed in, for example, above JP-B 51–32640 (corresponding to D.E. Patent 2,253,750 and U.S. Pat. No. 4,035,370) and above JP-B 2-27352 (corresponding to U.S. Pat. No. 4,400,514).

The compound of the formula (I) or a pharmaceutically acceptable salt thereof can be used by per se known methods as an inhibitor of Aβ production or secretion, in particular as an agent for preventing or treating Alzheimer's disease. For example, it can be administered orally or parenterally to mammals (e.g., mouse, rat, hamster, rabbit, cat, dog, cow, sheep, monkey and man) in various conventional dosage forms, such as tablets, granules, fine granules, capsules, injections, and suppositories.

For example, tablets can be prepared by granulating the medicine per se or a homogeneous mixture or it with an excipient, binder, disintegrator or other appropriate additives by appropriate methods, and then compress-shaping the resulting granules with a lubricant, etc., or by directly compress-shaping the medicine per se or a homogeneous mixture of it with an excipient, binder, disintegrator or other appropriate additives, or by compress-shaping previously-prepared granules or a homogeneous mixture of them with appropriate additives. If necessary, colorants, corrigents, etc., can be added to the composition. In addition, the composition may be coated with an appropriate coating agent.

Injections can be prepared by dissolving, suspending or emulsifying an appropriate amount of the medicine in an appropriate amount of an aqueous solvent such as water for injection, physiological saline, Ringer's solution, etc., or a nonaqueous solvent such as conventional vegetable oils, etc. Alternatively, injections can be prepared by filling an appropriate amount of the medicine into a vial for injection and sealing the vial.

Examples of carriers for oral compositions include materials commonly used in the art, such as starch, mannit, crystalline cellulose, carboxymethylcellulose sodium, etc. Examples of carriers for injections include distilled water, physiological saline, glucose solutions, transfusion solutions, etc. In addition, additives commonly used in the art can appropriately be added.

The dose varies with the subject disease, administration route, symptoms, etc. In general, it is 0.1 mg to 500 mg, preferably 1 mg to 100 mg, more preferably 1 mg to 20 mg, per day for a human adult.

Vinpocetine has been used as a medicament, and it has no toxic problems and can safely be administered.

As described above, the inhibitor of Aβ secretion or production of the invention is useful for treating or preventing brain disorders in mammals including humans. The subject diseases include, for example, senile dementia, Alzheimer's disease, cerebrovascular dementia, amyloid angiopathy, and Down's syndrome.

EXAMPLES

The following experiments and examples further illustrate the present invention in detail, but are not to be construed to limit the scope thereof.

Experiment 1

Inhibitory Activity against Aβ Production or Secretion in Human Neuroblastoma IMR-32 Cells 1) Materials and Methods Studies on Aβ production or secretion in human-derived neurons and gliocytes are very interesting because of the relation to Alzheimer's dementia. However, human primary culture neurons and gliocytes cannot generally be used for experimental materials. IMR-32 cells were therefore used. The IMR-32 cells are human-derived neuroblastoma cells, and produce and secrete Aβ in the culture supernatant (Shinkei Kagaku (Neurochemistry) 33, 232 (1994)). In addition, Dr. Hironobu Suzuki et al. (Science, 264, 1336 (1994)) had developed an enzyme immunoassay method that can determine and distinguish between Aβ of 40 amino acids (Aβ (1-40)) and Aβ of 42 amino acids (Aβ (1-42)). This method was used to determine inhibitory activity of the test compound against Aβ production or secretion.

a) Materials

Human neuroblastoma IMR-32 cells were purchased from American Type Culture Collection (ATCC). Dulbecco's modified Eagle's medium (DMEM) was purchased from Nissui Pharmaceutical Co., Ltd., Japan. Fetal calf serum (hereinafter sometimes abbreviated as FCS) and a mixed solution of penicillin (5000 U/ml) and streptomycin (5 mg/ml) were purchased from Biowhittaker Inc. Phosphate buffered saline (PBS) was purchased from Flow Laboratories. Block Ace was purchased from Dainippon Pharmaceutical Co., Ltd. Bovine serum albumin (BSA) was purchased from Sigma. Flasks for culture and 48-well multi well plates were those manufactured by Falcon and Coster Corporation, respectively. Standard samples of Aβ (1-40) and Aβ (1-42) were purchased from Bachem. The other reagents used were commercially available highest quality goods.

b) Methods

Culture of IMR-32 Cells

IMR-32 cells were cultured at 37° C. in 10% carbon dioxide/90% air using 10% FCS/DMEM culture solution in a flask (Falcon, 750 ml) until the confluent growth of the cells was obtained. Then, the cells were inoculated in a 48-well multi well plate at a density of $2.5 \times 10^5$ cells/well, and cultured for 5 days. The culture solution was sucked off, and then DMEM/0.5% BSA (0.5 ml for the assay of Aβ (1-40) or 0.25 ml for the assay of Aβ (1-42)) was added. The cells were cultured for 24 hours. The supernatant was sampled and stored at below −20° C. until use for the assay of Aβ.

Enzyme Immunoassay (EIA) of Aβ

FIG. 1 shows combinations of antibodies for the assay of Aβ (1-40) and Aβ (1-42). In each case, the primary antibody was BAN-50 antibody that recognizes the N-terminal region of Aβ (1-40). BA-27 is an antibody prepared using Aβ (1-40) as an antigen, and recognizes the C-terminal region of Aβ (1-40). On the other hand, BC-05 antibody is an antibody prepared using Aβ (35-43) as an antigen, and recognizes the C-terminal region of Aβ (1-42) but not Aβ (1-40). Therefore, Aβ (1-40) can be assayed with a combination of BAN-50 antibody with BA-27 antibody, and Aβ (1-42) can be assayed with a combination of BAN-50 antibody with BC-05 antibody.

A solution (100 μl/well) of BAN-50 antibody (15 μg/ml) in 0.1M carbonic acid buffer (pH 9.6) was added to a polyethylene microtiter plate, and the plate was allowed to stand at 4° C. overnight. The plate was rinsed with PBS three times, and a block solution (25% Block Ace/0.1% sodium azide/PBS) (200 μl) was added. The plate thus prepared was stored at 4° C. until use. The plate was rinsed with PBS three times, and a buffer for the primary reaction (20 mM phosphate buffer, pH 7.0; 400 mM NaCl; 2 mM EDTA; 10% Block Ace; 0.2% BSA; 0.05% sodium azide) (50 μl) was added. In addition, the standard samples (1000, 200, 40 and 8 pg/ml) (each 100 μl) diluted with the buffer for the primary reaction or the culture supernatant (100 μl) were added, and the mixture was allowed to stand at 4° C. overnight. After removal with suction, the plate was rinsed with PBS three times. A solution (100 μl) of a secondary antibody (BA-27 or BC-05 antibody) labeled with horseradish peroxidase (HRP) in a buffer for the secondary reaction (20 mM phosphate buffer, pH 7.0; 400 mM NaCl; 2 mM EDTA; 1% BSA). The reaction was carried out for 6 hours at room temperature, the plate was rinsed seven times, and a coloring reagent (TMB Peroxidase Substrate, Kirkegaard & Perry Lab.) (100 μl) was added. The reaction was carried out at room temperature for 8 to 10 minutes, and then stopped with 1M phosphate solution (100 μl). The mixture was subjected to colorimetry (wavelength: 450 nm) on a plate reader (Corona, MTP-32 Micro Plate Reader).

Evaluation of the Cytotoxicity (1) MTT Method

The culture supernatant was sampled, and DMEM culture solution (500 μl) containing 1.2 mM MTT {3-(4,5dimethyl- 2-thiazolyl)-2,5-diphenyl-2H-tetrazolium bromide} was added. The reaction was carried out for 1 hour at 37° C., and then an equal amount of 10% sodium dodecyl sulfate solution was added. The mixture was gently stirred overnight to dissolve the resulting formazan, and then subjected to colorimetry (wavelength: 550 nm) with a plate reader.

(2) Lactate Dehydrogenase (LDH) Method

The culture supernatant (10 μl) obtained after the assay of Aβ (1-40) was sampled, and the amount of LDH released from the cells was determined with a LDH assay kit (LDH C-II manufactured by Wako Pure Chemical Industries, Ltd.).

Statistical Analysis

Four wells were used per dose of the drug. The value in the data was represented as a ratio (%) to the control group. Dunnett's t test was used for the statistical analysis.

2) Results a) Standard Curve of Aβ (1-40) and Aβ (1-42)

Figure 2:
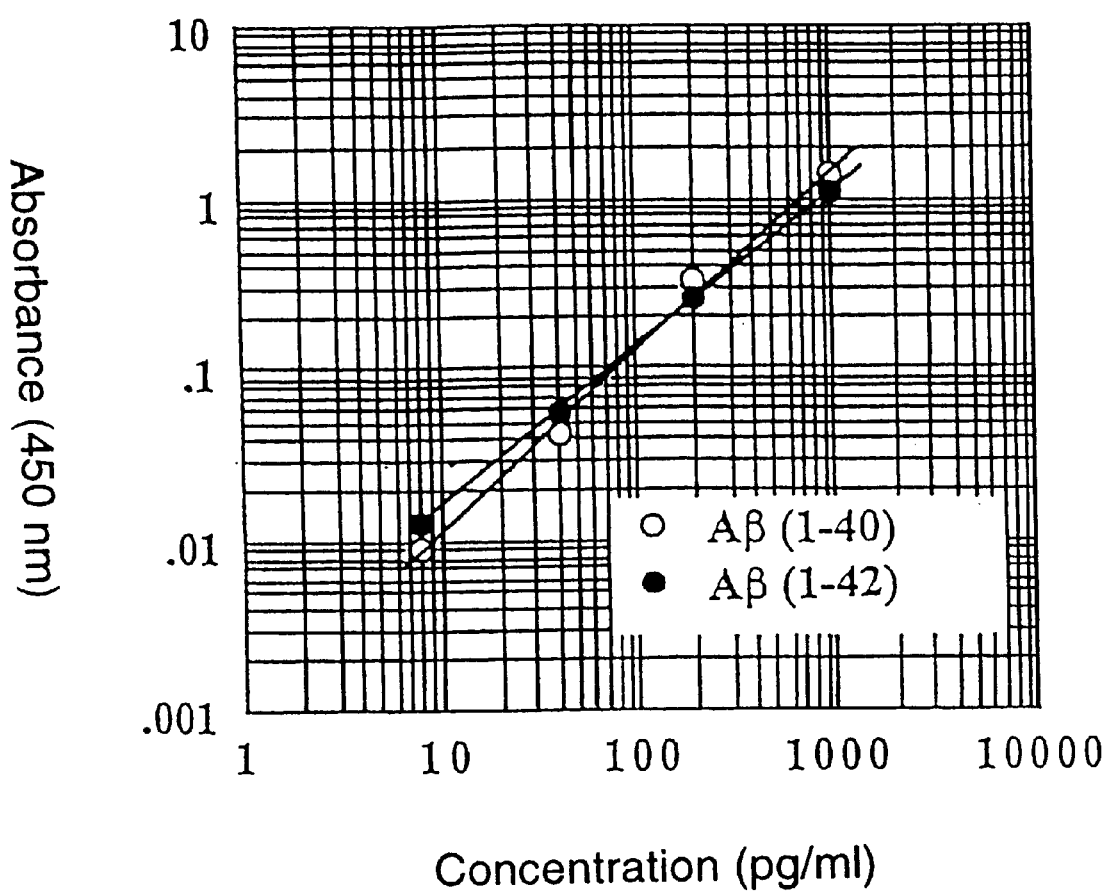
FIG. 2 shows a standard curve of the EIA system against Aβ (1-40) and Aβ (1-42).
Figure 3A:
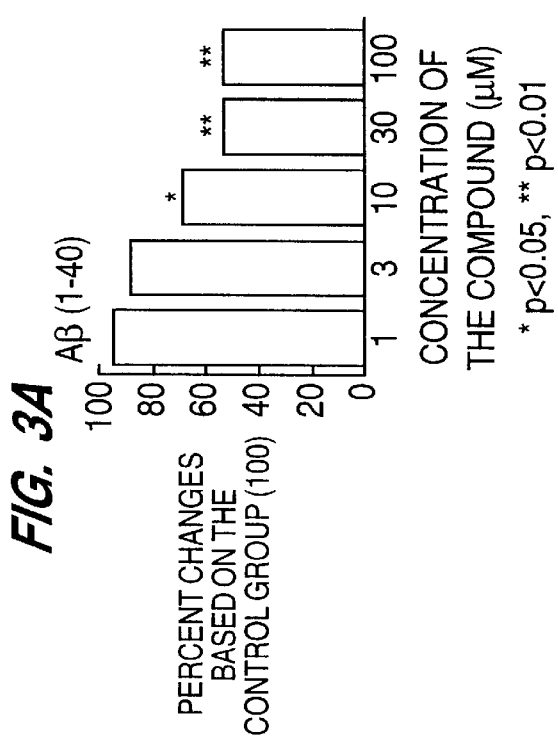
FIG. 3 represents graphs showing inhibitory activity of vinpocetine (i.e. the compound of the formula (II) wherein X is hydrogen and $R^4$ is ethyl) against Aβ production or secretion in human neuroblastoma IMR-32 cells. Each bar graph indicates the mean value with respect to 4 wells.
Figure 3B:
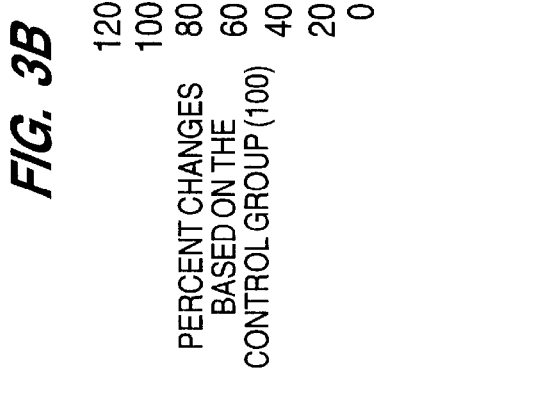
Figure 3C:
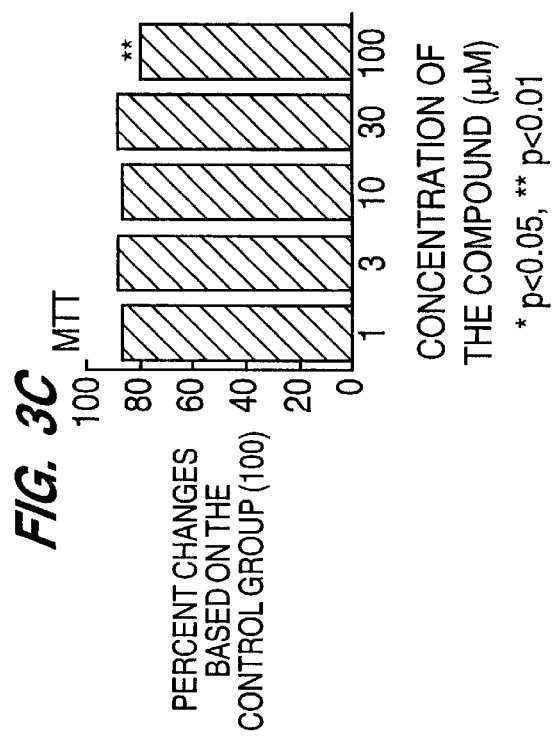
Figure 3D:
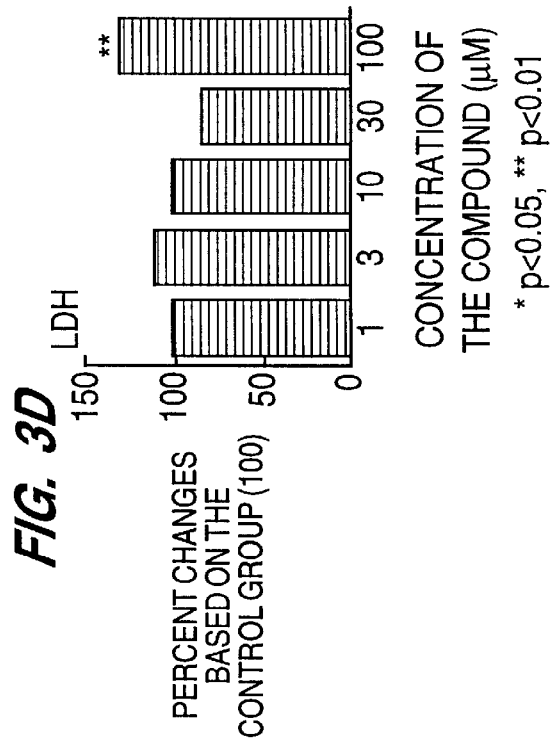

FIG. 2 shows a standard curve of the EIA system against the concentrations of Aβ (1-40) and Aβ (1-42). The assay was carried out in 8 pg/ml to 1000 pg/ml. In this range, the absorbance increased in proportion to the concentrations of Aβ (1-40) and Aβ (1-42). The detection limit of this method was about 10 pg/ml.

b) Effects of the Compound of the Formula (I) on the Production and Secretion of Aβ (1-40) and Aβ (1-42) from IMR32 Cells IMR-32 cells constantly produce and secrete Aβ. The amount of Aβ in the culture supernatant was measured. It was confirmed that Aβ (1-40) in not less than 500 pg/ml and Aβ (1-42) in an amount of not more than one tenth times the amount of Aβ (1-40) were produced and secreted under the culture conditions used in this experiment. Thus, the effects of the compound on the production and secretion were able to be evaluated by the determination of the amount of Aβ in the supernatant obtained after adding the compound.

FIG. 3 shows inhibitory activity of vinpocetine against production or secretion of Aβ.

Vinpocetine in $3\times10^{-6}$, $1\times10^{-5}$, $3\times10^{-5}$ and $1\times10^{-4}$M inhibited Aβ production or secretion by 10, 30, 40 and 45%, respectively, based on the control group. Aβ (1-42) production and secretion showed a tendency to decrease at $3\times10^{-6}$ and $1\times10^{-5}$M compared to the control group, but it was not a significant change. Presumably, this is partly because the amount of Aβ (1-42) production and secretion was very low and varied with the wells. In this case, the amount of formazan formed from MTT and LDH activity in the culture supernatant were determined as an indication of the cytotoxicity. The results showed only slight cytotoxicity at $1\times10^{-4}$, the maximum concentration used.

Experiment 2

Inhibitory Activity against Aβ Production and Secretion in Guinea Pig Primary Culture Neurons 1) Materials and Methods Cultivation of Neurons Fetal brains were taken out from guinea pigs (SLC-Hartley) that was 28 days pregnant. The cerebral cortex and hippocampus were taken out under a stereoscopic microscope, and, after removing the meninges, were treated in Hank's Balanced Salt Solution (20 ml) containing 0.25% trypsin/0.01% DNase I for 10 minutes. FCS was added to stop the reaction, and the mixture was centrifuged. The cells were dispersed in DMEM culture solution (DMEM/N2 culture solution) containing insulin 5 μg/ml, transferrin 100 μg/ml, progesterone 20 nM, putrescine 100 μM and sodium selenite 30 nM. The dispersion was filtered through double lens paper, and the filtrate was centrifuged to collect the cells. The cells were dispersed in DMEM/N2 culture solution, and inoculated in a 24-well plate at a density of $1\times10^{-6}$ cells/well. On the second day from the beginning of the cultivation, the culture solution was replaced with DMEM/N2 culture solution containing cytosine arabinoside (1 μM). After the treatment for 3 days, the culture solution was replaced with DMEM/N2 culture solution. Thereafter, the culture solution was replaced every 2 to 3 days. On the 12th day from the beginning of the cultivation, DMEM/N2 culture solution containing vinpocetine was added. After 24 hours, the culture supernatant was collected and stored at below −20° C. until use for the quantification of Aβ.

Enzyme Immunoassay of Aβ (EIA)

Aβ (1-40) and Aβ (1-42) in the culture supernatant were quantified in the same manner as that described in Experiment 1.

Evaluation of the Cytotoxicity

After the culture supernatant was collected, DMEM culture solution (300 μl) containing 1.2 mM MTT was added. After the reaction was carried out at 37° C. for 1 hour, an equal amount of 10% sodium dodecyl sulfate solution was added. Thereafter, the same procedure as that described in Experiment 1 was followed.

2) Results

Figure 4:
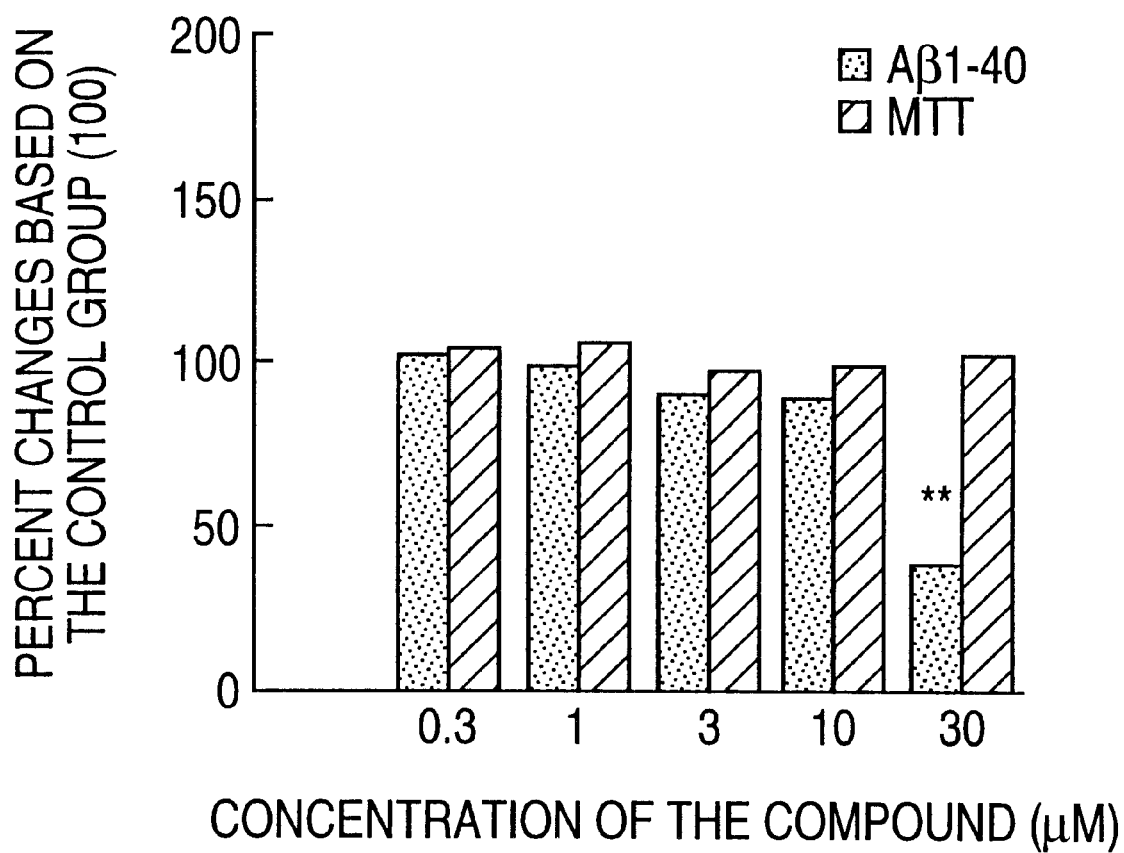
FIG. 4 is a graph showing inhibitory activity of vinpocetine against Aβ production or secretion in guinea pig primary culture neurons. Each bar graph indicates the mean value with respect to 4 wells.

FIG. 4 shows the results of the test for the inhibitory activity of vinpocetine against Aβ (1-40) production and secretion in neurons. Vinpocetine inhibited production or secretion of Aβ (1-40) in $3\times10^{-5}$M without any cytotoxicity. Because Aβ (1-42) was produced or secreted in a small amount, it was impossible to evaluate the inhibitory activity of vinpocetine against Aβ (1-42).

Example 1

| | |
|---|---|
| (1) Vinpocetine | 5.0 g |
| (2) Lactose | 82.5 g |
| (3) Hydroxypropylcellulose | 2.8 g |
| (4) Magnesium stearate | 0.4 g |
| (5) Hydroxypropylmethylcellulose 2910 | 2.994 g |
| (6) Corn starch | 19.3 g |
| (7) Macrogol 6000 | 0.6 g |
| (8) Titanium oxide | 0.4 g |
| (9) Iron sesquioxide | 0.006 g |

The ingredients (1) to (6) were mixed. From the mixture, 1000 raw tablets each containing 5 mg of vinpocetine and being 6.5 mm in diameter were obtained. The tablets were coated with the ingredients (7) to (9) to obtain film-coated tablets of 6.6 cm in diameter.

Example 2

| | |
|---|---|
| (1) Vinpocetine | 5 g |
| (2) Lactose-crystalline cellulose (granules) | 330 g |
| (3) D-mannitol | 29 g |
| (4) Low substituted hydroxypropylcellulose | 20 g |
| (5) Talc | 25 g |
| (6) Hydroxypropylcellulose | 50 g |
| (7) Aspartame | 3 g |
| (8) Dipotassium glycyrrhizinate | 3 g |
| (9) Hydroxypropylmethylcellulose 2910 | 30 g |
| (10) Titanium oxide | 3.5 g |
| (11) Yellow iron sesquioxide | 0.5 g |
| (12) Light anhydrous silicic acid | 1 g |

The ingredients (1), (3), (4), (5), (6), (7) and (8) were suspended or dissolved in purified water per se known methods, and the nucleus granules of the ingredient (2) were coated with the suspension or solution to obtain raw fine granules. The raw fine granules were coated with the ingredients (9) to (11) to obtain coated fine granules. They were mixed with the ingredient (12) to obtain vinpocetine fine granules (1%, 500 g). The fine granules are wrapped so that each wrapper contains about 500 mg of the fine granules.

We claim:

1. A method of preventing or treating Down's syndrome, which comprises administering to a patient in need thereof an effective amount of a compound of the formula (I):

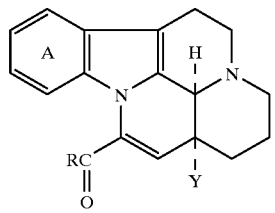

wherein ring A is an optionally substituted benzene ring, R represents $OR^1$,

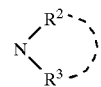

or $SR^1$, wherein $R^1$, $R^2$ and $R^3$ are the same or differentand each is selected from a hydrogen atom, an optionally substituted hydrocarbon group or $R^2$ and $R^3$, taken together with the adjacent nitrogen atom, form an optionally substituted nitrogen-containing heterocyclic group, and Y is an optionally substituted alkyl group, or a pharmaceutically acceptable salt thereof.

2. The method according to claim 1, wherein the ring A is a benzene ring which may have 1 to 3 substituents selected from halogen, R is $OR^1$ wherein $R^1$ is alkyl, and Y is ethyl.

3. The method according to claim 2, wherein the ring A is a benzene ring, and $R^1$ is ethyl.

4. The method according to claim 1, wherein the compound is administered in the form of a composition including a pharmaceutically acceptable excipient, carrier or diluent.

* * * * *